United States Patent [19]

Kent et al.

[11] Patent Number: 5,535,615
[45] Date of Patent: Jul. 16, 1996

[54] ABSORPTION TESTER FOR MEASURING THE WICKING CHARACTERISTICS OF A PAPERBOARD WEB

[75] Inventors: Henry J. Kent, Bloomingburg, N.Y.;
Yung B. Seo, Daejun, Rep. of Korea

[73] Assignee: International Paper Company, Tuxedo, N.Y.

[21] Appl. No.: 288,325

[22] Filed: Aug. 10, 1994

[51] Int. Cl.$^6$ .............................. G01N 15/08; G01N 5/02
[52] U.S. Cl. ................................... 73/38; 73/73; 162/263; 162/198
[58] Field of Search ........................ 73/38, 73; 162/198, 162/263

[56] References Cited

U.S. PATENT DOCUMENTS

| | | | |
|---|---|---|---|
| 2,755,660 | 7/1956 | Kammermeyer et al. | 73/38 |
| 2,861,451 | 11/1958 | Emmons III | 73/38 |
| 3,034,336 | 5/1962 | Upshur | 73/38 |
| 3,248,930 | 5/1966 | Speegle et al. | 73/38 |
| 3,466,925 | 9/1969 | Ziegenhagen et al. | 73/38 |
| 3,572,090 | 3/1971 | Graham et al. | 73/73 |
| 3,640,125 | 2/1972 | Girard et al. | 73/73 |
| 3,952,584 | 4/1976 | Lichstein | 73/73 |
| 4,357,827 | 11/1982 | McConnell | 73/73 |
| 4,385,517 | 5/1983 | Sorce et al. | 73/38 |
| 4,771,631 | 9/1988 | Lehtikoski et al. | 73/73 |
| 4,846,970 | 7/1989 | Bertelsen et al. | 73/38 |
| 4,976,138 | 12/1990 | Benninghoff et al. | 73/73 |
| 5,138,870 | 8/1992 | Lyssy | 73/38 |

FOREIGN PATENT DOCUMENTS

| | | | |
|---|---|---|---|
| 59645 | 2/1990 | Japan | 73/73 |
| 3-9809 | 1/1991 | Japan. | |
| 828015 | 5/1981 | U.S.S.R. | |
| 862073 | 9/1981 | U.S.S.R. | 73/73 |

*Primary Examiner*—Hezron E. Williams
*Assistant Examiner*—Daniel S. Larkin
*Attorney, Agent, or Firm*—Luedeka, Neely & Graham

[57] ABSTRACT

This invention relates to a method and apparatus for determining the wicking characteristics of a web, particularly a paperboard web with respect to a liquid. The apparatus comprises a web holder having an upper section, a lower section, an upper web seal attached to the upper section for sealing against a first surface of the web, a lower web seal attached to the lower section for sealing against a second surface of the web, and means for connecting the upper and lower sections together with the web disposed therebetween so the upper and lower seals sealingly engage the respective first and second surfaces of the web between the seals. The upper and lower sections define a chamber in the holder when connected together by the means for connecting so as to dispose one portion of the web in the chamber and another portion of the web external to the chamber so that the external portion of the web may be exposed to the liquid and the chamber isolated from the liquid by the sealing engagement of the seals with respect to the web. There is also provided a conduit in the holder in fluid flow communication with the chamber so that the chamber may be connected in fluid flow communication with a pressure source.

20 Claims, 5 Drawing Sheets

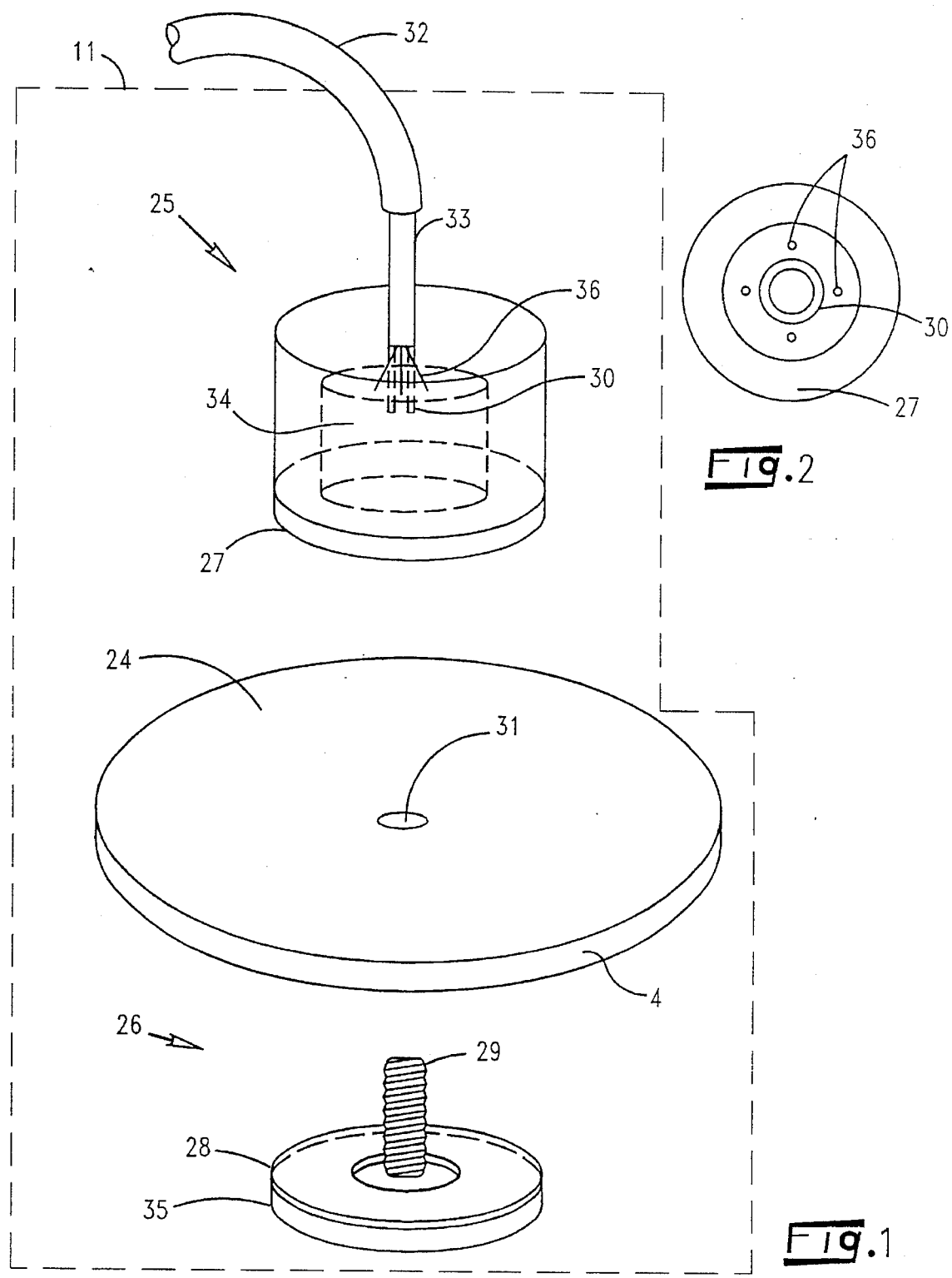

ABSORPTION TESTER FOR MEASURING THE WICKING CHARACTERISTICS OF A PAPERBOARD WEB

TECHNICAL FIELD

The present invention is directed to a web liquid absorption apparatus and method for determining the wicking characteristics of a web, particularly a paperboard web used for forming liquid containers.

BACKGROUND OF THE INVENTION

Many water or liquid impervious containers such as milk, orange juice and grapefruit juice cartons are manufactured by a process which involves folding a flat sheet of coated paperboard into a container shape. Since the blanks to be folded are typically cut from coated sheets of paperboard, at least one uncoated cut edge of the paperboard is typically exposed to the liquid in the formed container. Absorption of the liquid can occur at this uncoated cut edge while the carton is at rest or as a result of vibrational and other forces generated during shipping and handling. When the liquid penetrates or wicks through this uncoated edge the carton may lose structural strength and containment integrity and thus may leak. A method for testing coated paperboard in a paper mill environment is therefore beneficial as a quality control measure to assess the susceptibility of the paperboard to wicking and subsequent failure.

There are presently several methods and apparatus for determining the wicking properties of materials. One method involves inserting a doughnut-shaped web sample into a device so that only the cut edges of the web are in contact with a liquid in a chamber, filling the chamber and a calibrated capillary tube with the liquid, and measuring the rate at which the liquid is drawn down through the sample. In this method only ambient pressure is applied to the test liquid and chamber and there are no means for accelerating the test to reduce the testing time. Furthermore the test fails to provide a means for simulating vibrational forces generated during transportation and handling of paperboard containers. Additionally, this test method requires filling and emptying the liquid reservoir for each test.

It is, therefore, an object of the present invention to provide an improved web wicking apparatus and method for testing a web at its production site.

Another object of the present invention is to provide a simple web sample preparation method and mounting procedure for testing the wicking properties of a web.

A further object of the present invention is to provide computer automation of all phases of the test procedure, including overall assessment of the web's wicking characteristics.

An additional object of the present invention is to provide a test device and method adapted for use as a quality control measure for coated paperboard webs in a paper mill environment.

A still further object of the present invention is to provide an apparatus and method for simulating vibration levels that paperboard containers experience during shipping and handling.

SUMMARY OF THE INVENTION

Regarding the foregoing and other objects of the invention, the present invention provides a test apparatus for determining the wicking characteristics of a paperboard web with respect to a liquid. The apparatus comprises a web holder having an upper section, a lower section, an upper web seal attached to the upper section for sealing against a first surface of the web, a lower web seal attached to the lower section for sealing against a second surface of the web, and a means for connecting the upper and lower sections together with the web disposed therebetween. When so connected by the connecting means, the upper and lower seals sealingly engage the respective first and second surfaces of the web between the seals and the upper and lower sections define a chamber in the holder so as to dispose one portion of the web in the chamber and another portion of the web external to the chamber. The portion of the web external to the chamber may then be exposed to the liquid while the chamber is isolated from the liquid by the sealing engagement of the seals with respect to the web. There is also a conduit in the holder in fluid flow communication with the chamber so that the chamber may be connected in fluid flow communication with a pressure source.

In another preferred embodiment, this invention also provides a container for immersing the external portion of the web in the liquid. Once immersed, a pressure lower than a pressure external to the chamber is formed in the chamber by a pressure forming device which is in fluid communication with the conduit. A pressure sensing device in fluid communication with the chamber is also provided for sensing the pressure in the chamber. A weight detection device supports the container containing the liquid and detects the amount of liquid drawn into a paperboard web during the test. In order to isolate the web holder from the weight detection device, a web holder mounting device is provided for suspending the web holder and external portion of the web in the liquid.

Also provided is a data acquisition control and storage device interconnected with the pressure sensing device and the weight detection device for controlling and recording pressure changes within the chamber and for recording liquid weight changes. In a preferred embodiment, the application of chamber pressures, the sensing and recording of chamber pressures, and the detection and recording of liquid weights is automated by the use of a computer.

In a particularly preferred embodiment, this invention provides a method for testing the wicking properties of a web with respect to a liquid. The method comprises providing a web having a first surface and a second surface. The web is disposed in a web holder comprising an upper section, a lower section, an upper web seal attached to the upper section for sealing against the first surface of the web, a lower web seal attached to the lower section for sealing against the second surface of the web, and means for connecting the upper and lower sections together with the web disposed therebetween so that the upper and lower seals sealingly engage the respective first and second surfaces of the web between the seals. When so connected, the upper and lower sections define a chamber in the holder so that a portion of the web is disposed in the chamber and another portion of the web is disposed external to the chamber. There is also provided a conduit in the holder in fluid flow communication with the chamber for connecting the chamber to a pressure source.

Next the external portion of the web is immersed in a container containing the liquid. After immersion, one or a plurality of pressures are applied to the chamber whereby a portion of the liquid is drawn into the immersed portion of web. By sensing and recording the chamber pressure and detecting and recording changes in weight of the liquid, the wicking characteristics of the web can be determined.

BRIEF DESCRIPTION OF THE DRAWINGS

The invention will now be described in further detail with reference to the drawings wherein like reference characters designate like or similar elements throughout the several views as follows:

FIG. 1 is an isometric view of the web holder of this invention;

FIG. 2 is a bottom view of the upper section of the web holder illustrating apertures therein;

DETAILED DESCRIPTION OF THE PREFERRED EMBODIMENT

Figure 3:
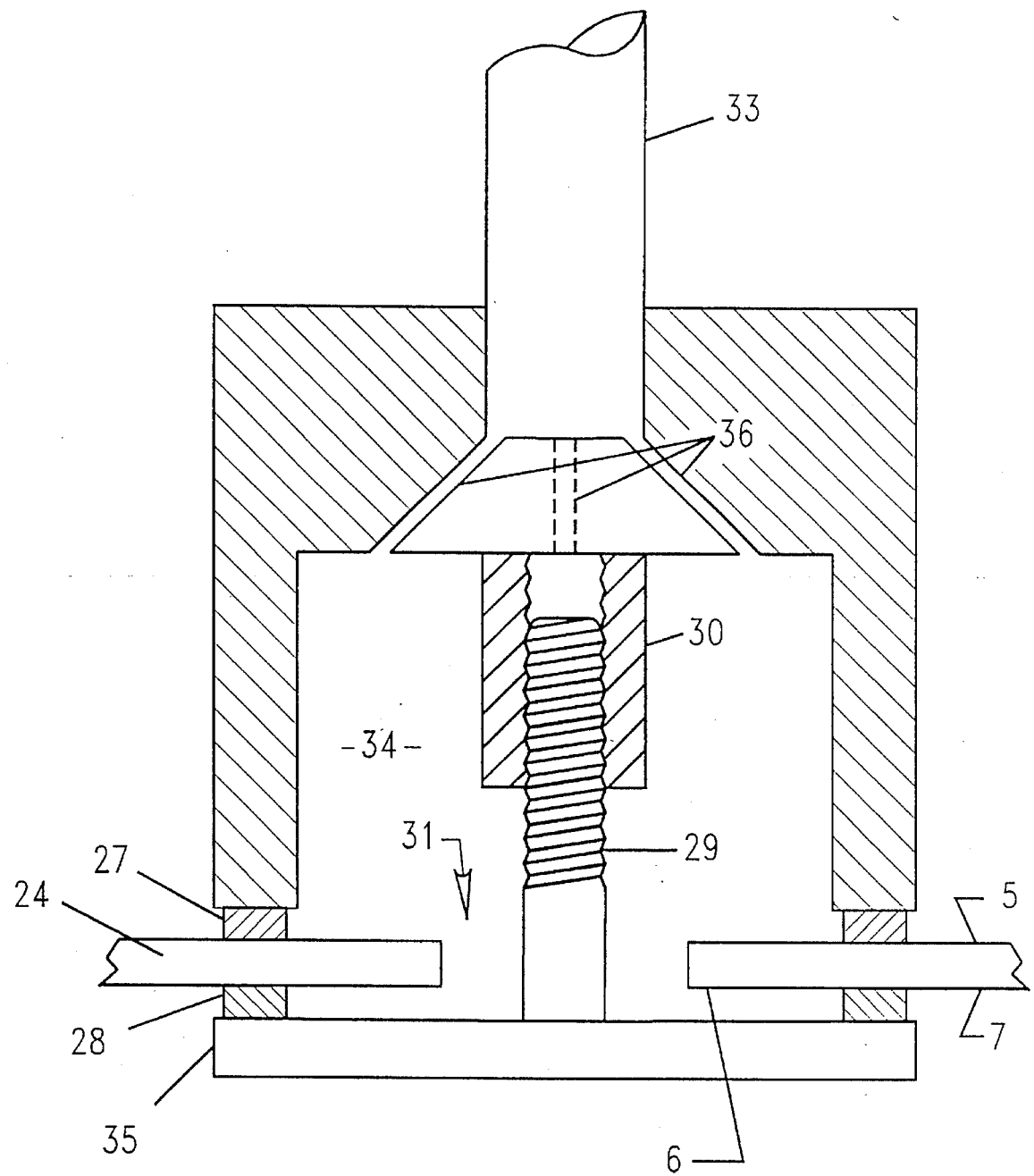
FIG. 3 is a cross-sectional view of the sample holder assembly.

In accordance with a preferred embodiment of the present invention as shown in FIGS. 1, 2 and 3, the web holder used in an apparatus for determining the wicking characteristics of a web is illustrated.

Figure 4:
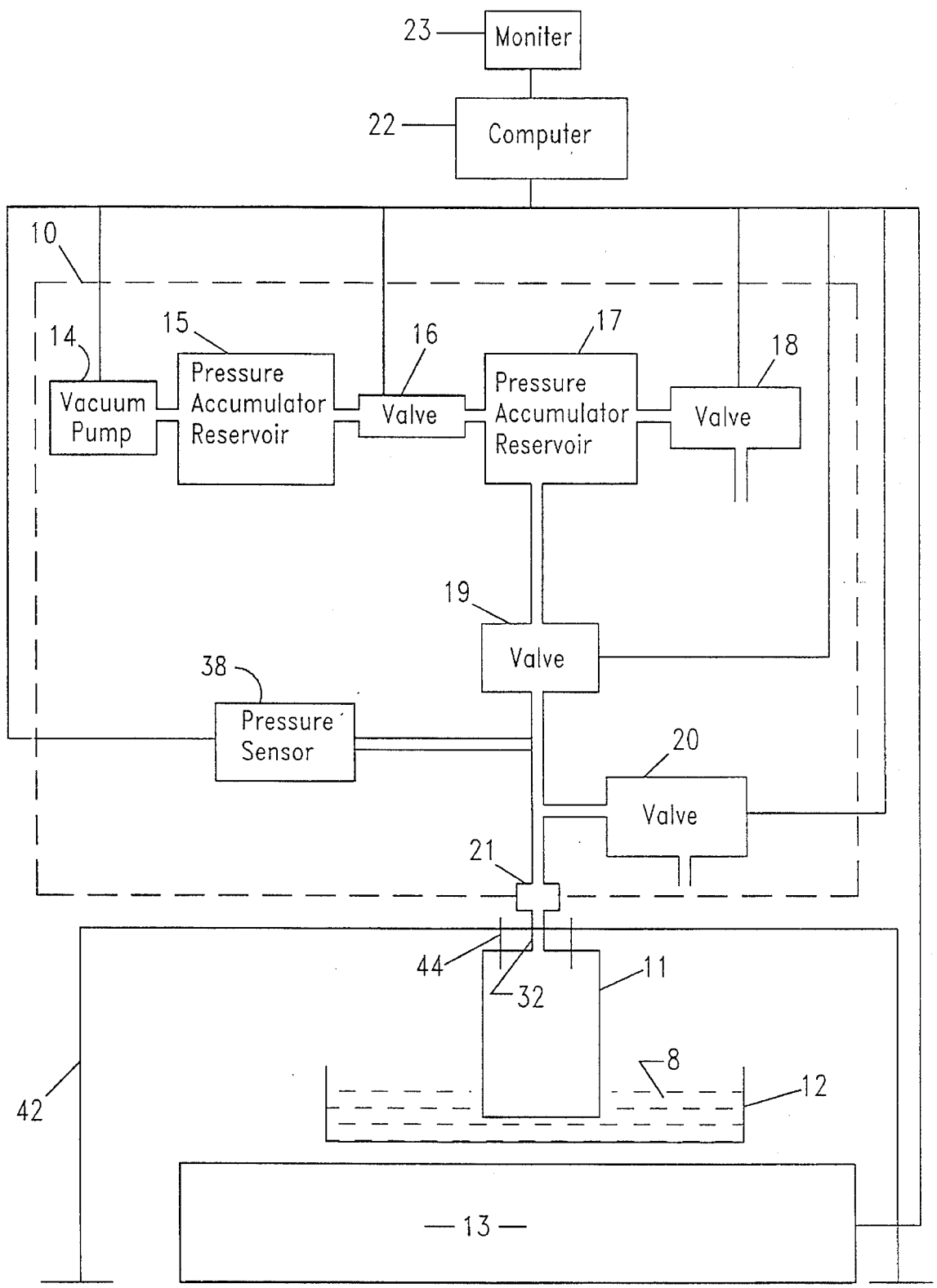
FIG. 4 is a functional block diagram of the invention.

The web holder 11 includes an upper section 25 and a lower section 26. Preferably the upper and lower sections are cylindrical in shape, but may be any shape which provides the functions provided by the web holder of this invention. The upper section 25 contains an upper web seal 27 such as a resilient ring gasket, a cavity defing a chamber 34 and apertures 36 in fluid flow communication with the chamber 34. The upper section also contains a rigid conduit 33 and a flexible conduit 32, such as a hose or tubing, one end of which is attached to the rigid conduit 33. Both the flexible conduit 32 and the rigid conduit 33 are in fluid flow communication with apertures 36 which are preferably arranged in a conical pattern in the upper section 25 of the holder. The opposite end of the flexible conduit 32 is preferably connected in fluid flow communication with a vacuum port 21 (FIG. 4). Directly beneath and in coaxial alignment with the rigid conduit 33 is a female threaded connector 30 extending downward into the chamber 34 (FIG. 3).

The lower section 26 of the web holder 11 includes an end cap 35, a resilient lower web seal 28 preferably having substantially the same dimensions as the upper web seal 27 which lower seal is attached to the end cap 35. Both the upper and lower web seals 27 and 28 may be formed from a reslient material for sealingly engaging the web at the webs first and second surfaces 5 and 7 (FIG. 3).

An upstanding male threaded connector 29 is attached to the end cap 35. The male threaded connector 29 and the female threaded connector 30 form a connecting means for the upper and lower sections of the web holder 11. It is of course possible to have the male threaded connector 29 extend from the upper section 25 and the female threaded connector 30 extend from the lower section 26. In the alternative, the upper and lower sections 25 and 26 may be connected by any other suitable means such as clamps external to the holder, screws or bolts through the upper and lower sections of the holder. Preferably the male connector 29 and female connector 30 have diameters smaller than the diameter of an opening 31 in a web 24 to be tested such that the threaded connectors of the connecting means can readily pass through opening 31.

With reference to FIG. 3, when male threaded connector 29 in the lower section 26 is mated with female threaded connector 30 in the upper section 25 and a web is disposed between the upper and lower sections such that the upper and lower seals 27 and 28 are sealingly engaged with the web, a fluid-tight chamber 34 is formed. The fluid-tight integrity of the seals can be ascertained before the testing procedure is begun by immersing the web 24 and web holder 11 in a liquid and using a syringe, gently pumping air through the web 24 from an outer web edge 4 (FIG. 1). If air bubbles are present at the interface between the upper and lower web seals 27 and 28 and the web 24, the upper and lower web seals 27 and 28 have not sufficiently formed a fluid-tight seal against the surfaces of the web 24. Adjustment of the securement device may be necessary to form such a fluid-tight seal.

Typically a paperboard web 24 to be tested is coated on both an upper surface 5 and a lower surface 7 while cut edges of the web 24, such as outer web edge 4 and inner web edge 6 remain uncoated. Since the inner web edge 6 is exposed to the pressure within the chamber 34, a lower pressure within chamber 34 will result in liquid absorption at the outer web edge 4 of the web 24 when the web 24 is immersed a liquid.

Figure 5:
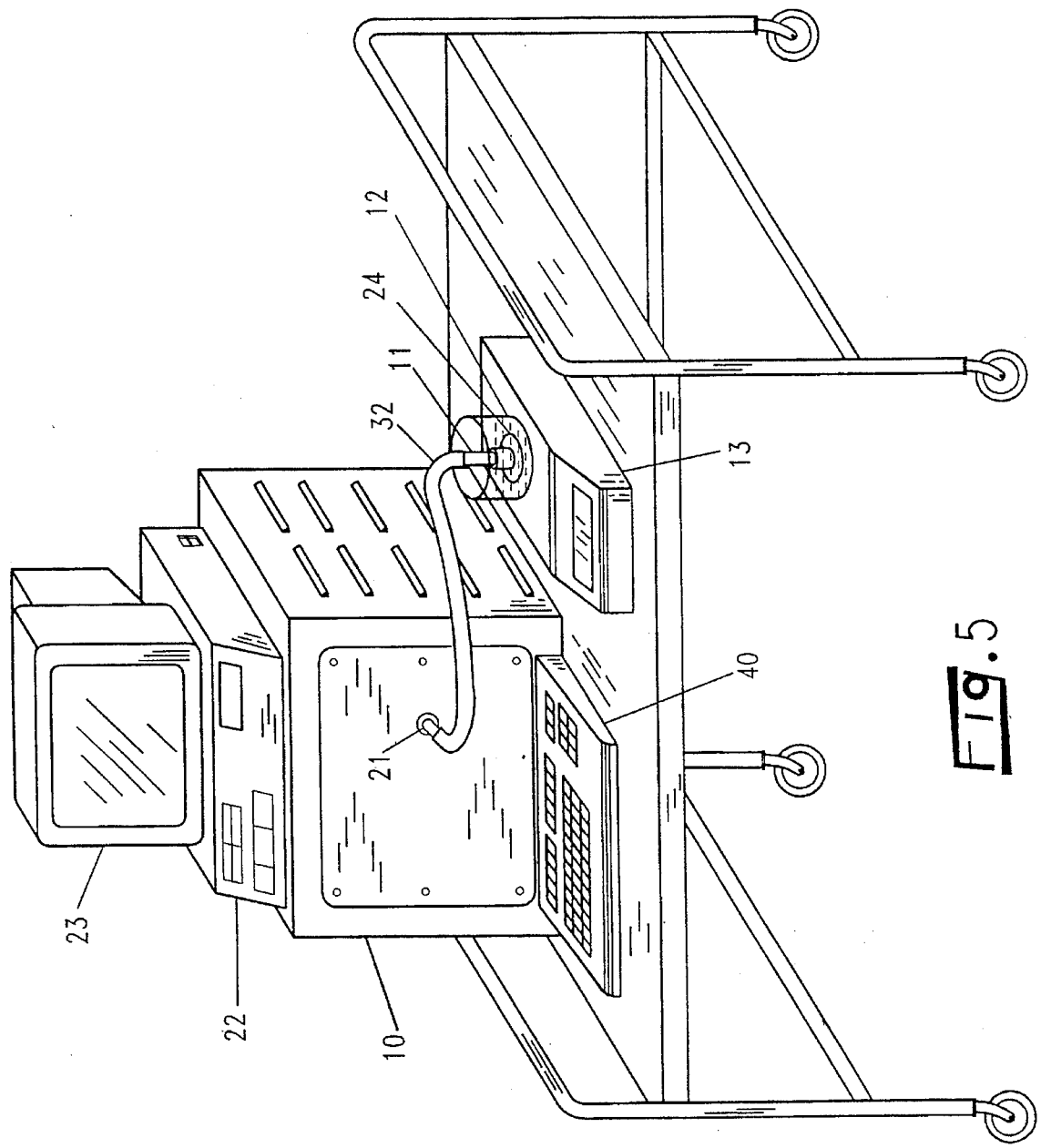
FIG. 5 is an overall illustration of the apparatus of this invention.

With reference to FIGS. 4 and 5, the apparatus of this invention thus illustrated includes a web holder 11, a pressure control system 10 attached via port 21 and conduit 32 to the web holder 11, a container 12 for containing a liquid 8, an electronic scale 13 preferably a high resolution electronic balance, and a computer 22, preferably an IBM AT compatible computer having a monitor 23 and input device 40 for controlling the pressure control system 10 and recording the weight from electronic scale 13. In a particularly preferred embodiment, the computer 22 is an Intel 80386-based PC running on MS-DOS. The computer 22 is configured to control a pressure source such as a vacuum pump 14 and valves 16, 18, 19 and 20 by means of, for example, a Keithley Metrabyte DASCON-1 I/O PC bus plug-in card. Switching of the pump and valves is accomplished, for example, by connecting the digital output lines from the DASCON-1 board to Magnecraft optically isolated solid state relays. The computer 22 receives data from the electronic scale 13, preferably a Sartorius electronic balance with a full scale capacity of 1.2 Kg and a resolution of 1 mg. Communication between computer 22 and scale 13 is via a standard RS-232 data bus. The pressure applied by the vacuum pump 14 is measured by means of pressure sensor 38 connected to an analog input on the DASCON-1 board. Analog to digital conversion of this signal is by means of a 12-bit ADC running at 16 Hz.

The pressure control system 10 also includes two pressure accumulation reservoirs 15 and 17 for smoothing pressure fluctuations and isolating the web 24 to be tested from pressure pulses emanating from the pressure source 14. Each of the pressure accumulation reservoirs 15 and 17 preferably have a capacity of approximately ten liters. For the purposes of this invention, all references to pressure include subatmospheric as well as superatmospheric pressures.

In order to isolate the web holder from the scale so that only liquid weight changes in container 12 are detected, the web holder is preferably attached to a web holder mounting device 42 via connectors 44. The web holder mounting device 42 may be of any configuration provided it effectively isolates the weight of the web holder 11 and web 24 from the scale 13. A particularly useful web holder mounting device may be in the form of a dome which is large enough to cover the scale 13 and liquid container 12 while suspending the web holder 11 and web 24 in the liquid 8. Such a device may also provide a closed-environment to reduce evaporation of liquid from container 12.

In operation, solenoid valve 16 is opened, and bleed valve 18, and solenoid valves 19 and 20 are initially closed and the vacuum pump 14 is started. As the pressure in the reservoirs 15 and 17 drops, the pressure is measured by the computer 22 at, for example, a 16 hertz rate. When the pressure in the system reaches a point about 5% lower than a target pressure, the vacuum pump 14 is automatically shut off, valve 16 is closed, and a bleed valve 18 is opened to slowly leak air into reservoir 17 to increase the pressure within reservoir 17 to the target pressure. When the target pressure is reached, bleed valve 18 closes, valve 19 opens to expose the web 24 being held in the web holder 11 to pressure in accumulator 17, and the computer 22 begins recording weights from the electronic scale 13. At the end of a preset period, as programmed into computer 22 by input device 40, valve 19 is closed and the cycle is repeated for the next preprogrammed pressure.

In operation, valve 20 may be preprogrammed to provide a number, intensity, and duration of pressure pulses to the web 24 to simulate the effects of motion and vibration during shipping of filled liquid packaging containers made from such paperboard webs. In order to provide such pressure pulses, when the target pressure in reservoir 17 is attained, valve 19 and valve 20 alternately open and close rapidly in a preprogrammed sequence. Opening valve 19 and closing valve 20 applies a pressure to the web 24 in chamber 34 (FIG. 3) lower than the pressure external to chamber 34, while closing valve 19 and opening valve 20 increases the pressure on the portion of the web 24 in chamber 34 (FIG. 3).

A container 12 containing a liquid 8, for example, water, orange juice, or milk, is placed on the scale 13. A sample of web such as paperboard web, is prepared and placed into the web holder 11. When the web is coated on both surfaces but not the cut edges, liquid absorption typically occurs only at the edge exposed to the liquid 8.

To prepare a coated web for testing, a section of paperboard is laminated on both sides with a waterproof laminate, typically a silicone release paper is used as the laminate. A hot press is first preheated to 85 degrees Celsius. One sheet of silicone release paper is placed on the press shiny side up. A paperboard web of 8 inches by 11 inches is placed on the release paper. Dry mounting adhesive film is then placed on the top of the paperboard. A second sheet of release paper is placed on top of the film, shiny side down. The press is then closed for 25 seconds. After a 2 minute cool-down period, the paperboard is turned over an the other side is laminated by the same procedure. The coated paperboard web is then placed in a punch press which cuts a 3.5 inch diameter disk sample with a 0.25 inch diameter opening at its center. As illustrated in FIGS. 1, and 3, the prepared web 24 is then placed in the web holder 11.

Returning to FIGS. 4 and 5, after the web sample 24 has been prepared and placed in the web holder 11, a test procedure may be selected from a menu displayed on the computer monitor 23. Test procedures are preferably preprogrammed through input device 40 and can be modified, stored, or deleted as desired. The procedures specify which pressures are to be applied during the course of the test, the number of different pressures to be used, and the duration for which liquid absorption will take place under each pressure condition. There may also be an option to apply a series of pressure pulses of a preset number, intensity, and duration to the web 24 in order to simulate the effects of motion and vibration during shipping of filled liquid packaging containers.

When the preprogrammed testing sequence is complete, Darcy plot imbibition slopes may be calculated for each pressure. These slopes may then be used to calculate a single number characterizing how readily the test liquid will penetrate the web 24. Calculation can also be performed by computer 22.

As described herein, operation of the web testing apparatus may be computer menu driven. A test procedure may be selected from the menu on a computer screen and thereby specify which pressures are to be applied during the course of a test, the number of different pressures to be used, and the duration for which liquid absorption will take place under each pressure condition. There is also an option to apply a series of pressure pulses, the quantity, duration, and intensity of which may be selectable from the menu. As noted previously, this "pulsed mode" of testing may be used to simulate the effects of motion and vibration during shipping of filled liquid packaging containers. Once a particular test sequence has been selected, that sequence can be stored in the computer and reused in the future eliminating unnecessary duplicative programming. Those skilled in the art can readily program computer 22 for any test procedure or sequence desired.

Figure 6:
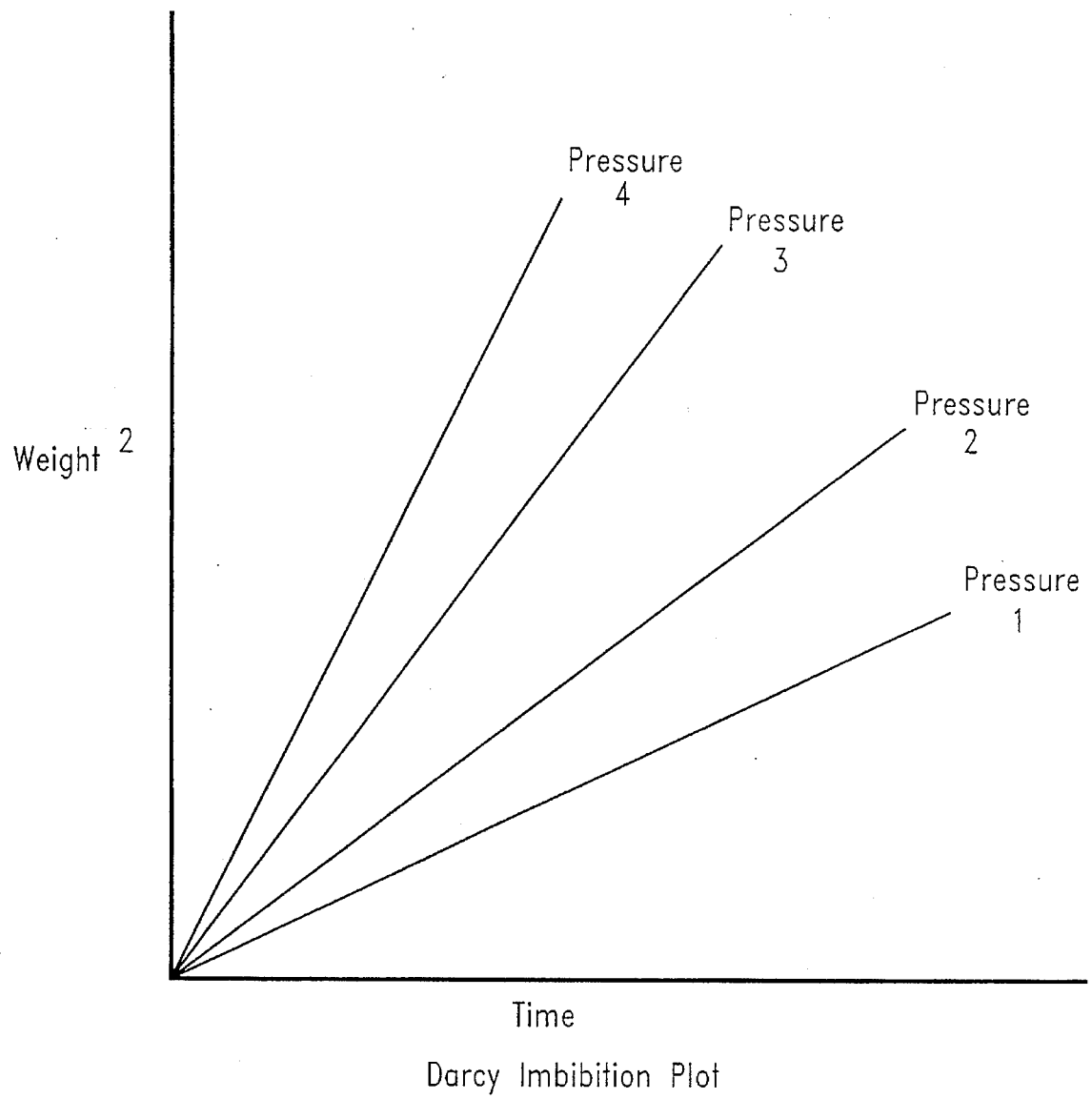
FIG. 6 is a graphical representation of a Darcy imbibition plot for several different pressures.

Having selected the test pressure sequence, the computer runs the test sequence, controlling pressures and continuously reading the electronic balance to determine the quantity of liquid being absorbed by the web sample. Once the preprogrammed sequence of measurements has been completed, Darcy plot imbibition slopes (FIG. 6) may calculated for each pressure and these values then processed to provide a single number characterizing how readily the test liquid will penetrate the web.

It is contemplated, and will be apparent to those skilled in the art from the preceding description and accompanying drawings that modifications and/or changes may be made in the embodiments of the invention. Accordingly, it is expressly intended that the foregoing description and accompanying drawings are illustrative of preferred embodiments only, not limiting thereto, and that the true spirit and scope of the present invention can be determined by reference to the appended claims.

What is claimed is:

1. A test apparatus for determining the wicking characteristics of a paperboard web with respect to a liquid, comprising: a web holder having an upper section, a lower section, an upper web seal attached to the upper section for sealing against a first surface of the web, a lower web seal attached to the lower section for sealing against a second surface of the web, means for connecting said upper and lower sections together with the web disposed therebetween so said upper and lower seals sealingly engage the respective first and second surfaces of the web between the seals, said upper and lower sections defining a chamber in the holder when connected together by said means for connecting as aforesaid so as to dispose one portion of the web in the chamber and another portion of the web external to the chamber so that the external portion of the web may be exposed to the liquid and the chamber isolated from the liquid by the sealing engagement of said seals with respect to the web, a conduit in said holder in fluid flow communication with the chamber so that the chamber may be connected in fluid flow communication with a pressure source and a container supported independently of said web holder containing a supply of a wicking liquid in contact with at least a portion of the external portion of the web.

2. The apparatus of claim 1 further comprising a pressure source connected in fluid flow communication with said conduit for applying a subatmospheric pressure in the chamber.

3. The apparatus of claim 1 further comprising a pressure sensing device in fluid flow communication with said chamber for sensing the pressure in said chamber.

4. The apparatus of claim 1 further comprising a web holder mounting device for suspending said web holder in the liquid so as to immerse said external portion of the web in the liquid.

5. The apparatus of claim 4 further comprising a weight detecting device for supporting the container and for detecting the weight of liquid in the container.

6. An automated test apparatus for determining the wicking characteristics of a paperboard web with respect to a liquid, comprising:
   a web holder having an upper section, a lower section, an upper web seal attached to the upper section for sealing against a first surface of the web, a lower web seal attached to the lower section for sealing against a second surface of the web, means for connecting said upper and lower sections together with the web disposed therebetween so said upper and lower seals sealingly engage the respective first and second surfaces of the web between the seals, said upper and lower sections defining a chamber in the holder when connected together by said means for connecting as aforesaid so as to dispose one portion of the web in the chamber and another portion of the web external to the chamber so that the external portion of the web may be exposed to the liquid and the chamber isolated from the liquid by the sealing engagement of said seals with respect to the web, and a conduit in said holder in fluid flow communication with the chamber so that the chamber may be connected in fluid flow communication with a pressure source;
   a container supported independently of said web holder containing a supply of liquid in contact with at least a portion of said external portion of the web;
   pressure source connected in fluid flow communication with said conduit for forming a subatmospheric pressure in the chamber;
   a pressure sensing device in fluid flow communication with said chamber for sensing the pressure in said chamber;
   a web holder mounting device for suspending said holder in the liquid so as to immerse said external portion of the web in the liquid;
   a weight detection device for supporting the container and for detecting the weight of liquid in the container; and
   a data acquisition control and storage device interconnected with said pressure sensing device and said weight detection device for controlling and recording pressure changes within the chamber and for recording liquid weight changes.

7. The apparatus of claim 6 wherein the weight detection device is an electronic scale.

8. The apparatus of claim 6 wherein the pressure source is a vacuum pump.

9. The apparatus of claim 6 wherein the pressure sensing device is a pressure transducer for generating an electronic analog signal.

10. The apparatus of claim 6 wherein the data acquisition control and storage device is a computer.

11. The apparatus of claim 8 further comprising a pressure isolating device for isolating a pressure accumulating device from said vacuum pump.

12. A method for testing the wicking properties of a web with respect to a liquid comprising:
    providing a web having a first surface and a second surface;
    disposing said web in a web holder comprising an upper section, a lower section, an upper web seal attached to the upper section for sealing against the first surface of the web, a lower web seal attached to the lower section for sealing against the second surface of the web, means for connecting said upper and lower sections together with the web disposed therebetween so said upper and lower seals sealingly engage the respective first and second surfaces of the web between the seals, said upper and lower sections defining a chamber in the holder when connected together by said means for connecting as aforesaid so that a portion of the web is disposed in the chamber and another portion of the web is disposed external to the chamber, and a conduit in said holder in fluid flow communication with the chamber for connecting the chamber to a pressure source;
    immersing the portion of web external to said chamber in a container containing a liquid;
    applying one or a plurality of pressures to said chamber whereby a portion of said liquid is drawn into said immersed portion of web;
    sensing and recording said chamber pressure;
    detecting and recording changes in weight of said liquid.

13. The method of claim 12 further comprising calculating a Darcy plot imbibition slope for each pressure applied to said chamber.

14. The method of claim 12 further comprising controlling said pressures and recording said pressures and weights with a computer.

15. The method of claim 12 wherein said weight changes are detected by an electronic scale.

16. A web holder for determining the wicking characteristics of a web with respect to a liquid comprising an upper section, a lower section, an upper web seal attached to the upper section for sealing against a first surface of the web, a lower web seal attached to the lower section for sealing against a second surface of the web, means for connecting said upper and lower sections together with the web disposed therebetween so said upper and lower seals sealingly engage the respective first and second surfaces of the web between the seals, said upper and lower sections defining a chamber in the holder when connected together by said means for connecting as aforesaid so as to dispose one portion of the web in the chamber and another portion of the web external to the chamber so that the external portion of the web may be exposed to the liquid and the chamber isolated from the liquid by the sealing engagement of said seals with respect to the web, and a conduit in said holder in fluid flow communication the chamber so that the chamber may be connected in fluid flow communication with a pressure source wherein said upper and lower seals are formed from resilient rings of substantially similar dimensions.

17. The web holder of claim 16 wherein the means for connecting comprises an upstanding threaded member and a threaded opening for engaging said threaded member.

18. The web holder of claim 16 wherein said conduit comprises a plurality of conically disposed apertures in said upper section.

19. The web holder of claim 16 wherein said upper and lower sections are cylindrically shaped.

20. The web holder of claim 16 wherein said chamber is cylindrically shaped.

* * * * *